United States Patent [19]

Izumi

[11] 4,392,387
[45] Jul. 12, 1983

[54] SAMPLING DEVICE FOR ANALYZING GAS WITH HIGH DUST CONTENT

[75] Inventor: Naoe Izumi, Mie, Japan
[73] Assignee: NGK Insulators, Ltd., Nagoya, Japan
[21] Appl. No.: 253,918
[22] Filed: Apr. 14, 1981
[30] Foreign Application Priority Data
  Apr. 28, 1980 [JP] Japan .............................. 55-58448[U]
[51] Int. Cl.³ ............................................. G01N 1/24
[52] U.S. Cl. ................................................ 73/863.21
[58] Field of Search ........... 73/863.12, 863.21, 863.24, 73/864.73

[56] References Cited

U.S. PATENT DOCUMENTS 2,895,335  7/1959  Kraftson et al. ................. 73/863.12
3,592,562  7/1971  Spliethoff ......................... 73/863.12
3,759,087  9/1973  Iwoa ................................ 73/863.12

Primary Examiner—S. Clement Swisher
Attorney, Agent, or Firm—Parkhurst & Oliff

[57] ABSTRACT

The disclosed sampling device has a gas suction tube through which gas with a high content of dust is sucked into the sampling device so as to cleanse the gas with water in the sampling device before analyzing the gas. At least one air nozzle is provided in the gas suction tube in such a manner that the air nozzle faces the inside surface of the gas suction tube wall and is directed toward the inlet opening of the gas suction tube, so that dust and other deposits sedimented on the inside surface of the gas suction tube is cleansed by air jets ejected from the air nozzle.

5 Claims, 1 Drawing Figure

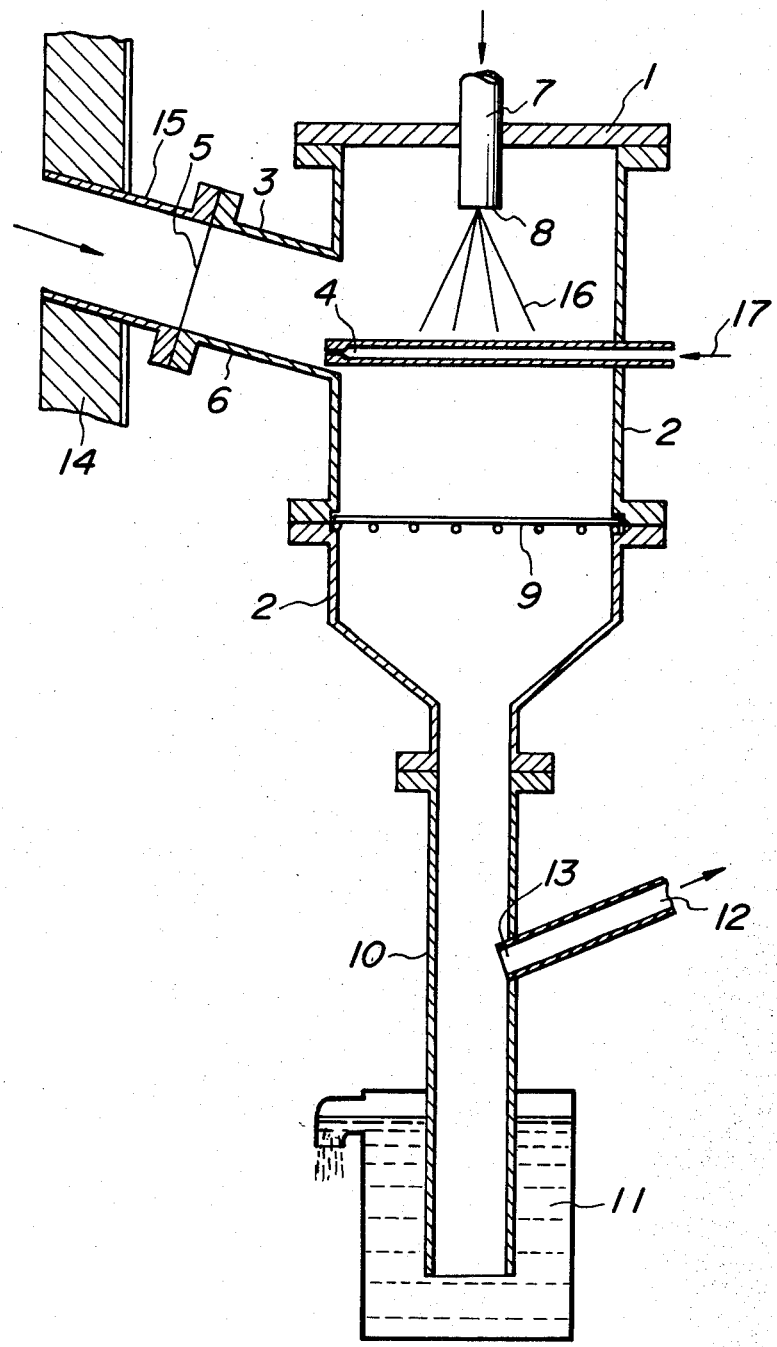

SAMPLING DEVICE FOR ANALYZING GAS WITH HIGH DUST CONTENT

BACKGROUND OF THE INVENTION

1. Field of the Invention

This invention relates to a sampling device to extract gas for various analyses from a source of gas with a high dust content.

2. Description of the Prior Art

In various combustion furnaces and boilers, such as incinerators to burn sewage sludge and the like, pyrolysis furnaces, coal or oil burning boilers of thermal power plants, and other furnaces, it has been generally practiced to control the combustion by analyzing the combustion exhaust gas therefrom so as to optimize the combustion based on data obtained by the analysis. The analysis includes measurement and detection of the concentration of combustibles, the oxygen concentration, the concentration of nitrogen oxides, and the concentrations of other components of the exhaust gas. When the combustion exhaust gas contains dust particles or sedimentary components, if such exhaust gas is directly introduced into various analytical apparatuses, the dust particles and the sedimentary components tend to deposit in the anayltical apparatuses, whereby the accuracy of the analysis is reduced and in extreme cases, the analysis becomes impossible due to plugging or clogging with the deposits of dust and the like.

To avoid the aforesaid deposits, gas sampling probes with suitable filters mounted thereon are sometimes used, so as to apply the exhaust gas to the analytical apparatuses only after removing the dust particles therefrom.

However, when the content or concentration of the dust particles or sedimentary components such as tar in the exhaust gas is high, the filter of the probe is apt to be fully plugged in a very short time, so that the probe of the prior art has shortcomings in that the filter must be replaced frequently and that continuous measurement is not possible.

To solve the shortcomings, when the exhaust gas contains a large amount of dust particles or tar components, it has been practiced to wash the exhaust gas with water to capture the dust particles or tar components by the water before analyzing the gas. However, the content in the exhaust gas is sometimes very high, for instance in the cases of coal burning boilers of thermal power plants which currently attract much attention from the standpoint of petroleum saving, incinerators of sewage sludge, pyrolysis furnaces for sewage sludge, and cement burning kilns. More specifically, when the dust content in the exhaust gas is 50 g/Nm$^3$ or more, the piping for extracting the exhaust gas for analysis is apt to be plugged by dust particles in a short time, so that various inconveniences and shortcomings are caused such as the need mechanical means to remove the dust deposits at uniform time intervals or the need of replacement of the exhaust gas extracting pipings.

SUMMARY OF THE INVENTION

Therefore, an object of the present invention is to obviate the aforesaid shortcomings of the prior art, by providing an improved sampling device for analyzing gas with a high dust content. The sampling device of the present invention is particularly suitable for extracting sample gas for various anaylses from exhaust gas containing a very large amount of tar and/or dust particles, such as exhaust gases from the aforesaid coal or oil burning boilers of thermal power plants, the incinerators of sewage sludge, the pyrolysis furnaces, the cement burning kilns, and the like.

To fulfil the aforesaid object, a sampling device for analyzing gas with a high dust content according to the present invention comprises a generally closed housing, a gas suction tube of comparatively large diameter connected to an upper portion of the housing so as to lead the gas with the high dust content into the housing, an air-jet nozzle disposed in the gas suction tube at a position close to joint between said gas suction tube and said housing, said air-jet nozzle facing inside wall surface of said gas suction tube and being directed toward inlet opening of said gas suction tube, a water supply conduit disposed at a top portion of said housing so as to supply water particles for cleansing the gas with the high dust content led into said housing, a screen disposed at a lower portion of said housing, a water sump connected to a bottom portion of said housing through a pipe, and a washed-gas passage having one end thereof connected to said pipe and an opposite end thereof communicated with the outside of the housing so as to lead the washed gas toward an analytical apparatus.

In an embodiment of the invention, an atomizer nozzle is secured to the lower end of the water supply conduit, so as to supply atomized water particles to the inside of the housing.

BRIEF DESCRIPTION OF THE DRAWING

For a better understanding of the invention, reference is made to the accompanying drawing, in which:

The single drawing is a schematic sectional view showing an embodiment of the sampling device for gas analysis according to the present invention.

In the FIG. 1 is a top cover, 2 is a housing, 3 is a gas suction tube, 4 is an air-jet nozzle, 5 is a gas inlet opening, 6 is tube wall, 7 is a water supply conduit, 8 is an atomizer nozzle, 9 is a screen, 10 is a pipe, 11 is a water sump, 12 is a washed-gas passage, 13 is a visor, 14 is a furnace, 15 is a pipe, 16 is atomized water, and 17 is high-pressure air.

DESCRIPTION OF THE PREFERRED EMBODIMENT

Referring to the embodiment illustrated in the single drawing, a top cover 1 tightly closes the upper end of the housing 2. A gas suction tube 3 of comparatively large diameter, such as an inside diameter of more than 40 mm, preferably about 100 mm, is connected to an upper portion of sidewall of the housing 2. At least one air-jet nozzle 4 is connected to the inside of the gas suction tube 3 in the proximity of the joint between the gas suction tube 3 and the housing 2. The air-jet nozzle 4 faces tube wall 6 of the gas suction tube 3 and is directed toward the inlet opening 5 of the tube 3.

Although only one air-jet nozzle 4 is shown, two or more air-jet nozzles 4 may be disposed along an inner circumferential surface of the gas suction tube 3.

A water supply conduit 7 is connected to the top cover 1, so that the gas with the high dust content led into the inside of the housing 2 through the gas suction tube 3 is washed by water particles injected into the housing 2 through the conduit 7. In the illustrated embodiment, an atomizer nozzle 8 is secured to the lower end of the water supply conduit 7, so as to wash the gas by atomized water paticles. A screen 9 of lattice structure is detachably secured to a lower portion of the housing 2, which screen is mainly for temporary holding of dust particles or solidified tar deposits peeled off from the inside surface of the gas suction tube 3 by air jets from the air-jet nozzle 4.

The bottom portion of the housing 2 communicates with a water sump 11 through a pipe 10. A washed-gas passage 12 has one end thereof connected to the pipe 10, while the opposite end of the washed-gas passage 12 is connected to the outside of the sampling device for instance to a suction pump (not shown) and an analyzing apparatus (not shown).

Preferably, a visor 13 is formed at the junction of the pipe 10 with the washed-gas passage 12 in such a manner that suction of moisture toward the washed-gas passage 12 is minimized.

In the preferred embodiment, the mesh of the aforesaid screen 9 is smaller than the inside cross secton of the pipe 10, and the direction of jetting air from the air-jet nozzle 4 makes an angle of about 15 to 30 degrees relative to the longitudinal axial direction of the gas suction tube 3.

The total cross sectional area of the air-jet nozzle or nozzles 4 should not exceed 10% of the cross sectional area of the gas suction tube 3, so that the gas suction tube 3 should not be plugged at the position where the air-jet nozzle 4 is disposed.

The operation of the sampling device of the aforesaid construction according to the present invention will be explained now. The sampling device is disposed close to a furnace 14 and the gas suction tube 3 is connected to the inside of the furnace 14 either by directly inserting the tube 3 therein or by coupling the tube 3 to a pipe 15 fixed to the furnace 14 therefor. Sampling of the gas from the inside of the furnace 14 is started by actuating a suction pump means (not shown) connected to the washed-gas passage 12. Thereby, the exhaust gas of the furnace 14, i.e., a gas with a high dust content, is sucked into the inside of the housing 2 through the gas suction tube 3. The thus sucked exhaust gas is washed by atomized water 16 from the water supply conduit 7, so that the tar components and dust particles of the exhaust gas are removed by being caught by the washing water. The tar components and the dust particles thus removed drop together with the water particles into the water sump 11 through the bottom portion of the housing 2 and the pipe 10. The tar components and the dust particles are then forwarded to a waste water treating device (not shown) together with the overflow of the water sump 11. On the other hand, the exhaust gas thus washed by atomized water 16 is sucked into the washed-gas passage 12 which is branched from the pipe 10, and the washed gas is delivered to a suitable analyzing apparatus (not shown). If necessary, the washed gas may be further treated before reaching the analytical apparatus, for instance by a dehumidifier or a fine filter (not shown).

To remove deposits of tar components and dust particles which are sedimented on the tube wall 6 of the gas suction tube 3 after using the sampling device for a long period of time, the delivery of the washed gas to the analytical apparatus (not shown) is halted and high-pressure air 17 is jetted from the air-jet nozzle 4 toward the tube wall 6 of the gas suction tube 3. The direction of the air jet from the nozzle 4 is reverse to that of the gas extraction from the furnace 14. The deposits on the tube wall 6 are peeled off by the jets of the high-pressure air 17, and the thus peeled deposits are removed and sucked into the inside of the housing 2 together with the exhaust gas and drop onto the screen 9. The atomized water 16 breaks down the deposits on the screen 9 into fine pieces. The fine pieces of the deposits thus formed are carried by the washing water into the water sump 11 through the pipe 10.

Thus, the deposits sedimented on the tube wall 6 can be easily removed, so that the analysis on the washed gas can be resumed quickly. It should be noted that plugging of the gas suction tube 3 can be prevented by periodic cleansing by the jetting of the high-pressure air 17 from the air-jet nozzle 4, so that stable and reliable operation of the sampling device can be ensured for a long period of time.

As described in the foregoing, the sampling device of the present invention is very simple in construction and yet capable of complete removal of tar components and dust particles from an exhaust gas or any gas with a high dust content. Even if deposits are sedimented on the tube wall of the gas suction tube, such deposits can be easily removed by reverse jetting of high-pressure air, so that stable operation of the sampling device can be maintained for a long time. The sampling device of the present invention is particularly suitable for analysis of exhaust gas with a high dust content, such as exhaust gas from coal or oil burning boilers of thermal power plants, incinerators of sewage sludge, pyrolysis furnaces, cement burning kilns, and other furnaces producing large amounts of dust particles. Thus, the sampling device for analyzing gas according to the present invention is very useful in industries.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. A sampling device for analyzing gas with a high dust content, comprising a generally closed housing (2), a gas suction tube (3) of a large diameter connected to an upper portion of the housing so as to lead the gas with the high dust content into the inside of the housing, an air-jet nozzle (4) disposed in said gas suction tube (3) in the proximity of joint between said tube (3) and said housing (2), said nozzle (4) facing tube wall (6) of said gas suction tube (3) and being directed toward inlet opening (5) thereof, a water supply conduit (7) connected to a top portion of said housing (2) so as to supply water for washing the gas with the high dust content led into the housing (2), a screen (9) disposed at a lower portion of said housing (2), a water sump (11) connected to a bottom portion of said housing (2) through a pipe (10), and a washed-gas passage (12) having one end thereof connected to said pipe (10) and an opposite end thereof communicated with outside of the sampling device.

2. A sampling device as set forth in claim 1, wherein said sampling device further comprises an atomizer nozzle (8) secured to lower end of said water supply conduit (7) so as to supply atomized water particles into the inside of the housing (2).

3. A sampling device as set forth in claim 1, wherein said sampling device further comprises a visor disposed at joint between said pipe (10) and said washed-gas passage (12) so as to prevent the water from entering into said washed-gas passage (12).

4. A sampling device as set forth in claim 1, wherein said sampling device comprises a plurality of said air-jet nozzles (4) disposed along inner circumferential surface of said gas suction tube (3).

5. A sampling device as set forth in claim 1, wherein said air-jet nozzle (4) is adapted to eject an air jet at an angle of 15 to 30 degrees relative to longitudinal axial direction of said gas suction tube (3).

* * * * *